United States Patent
Kawamura (10) Patent No.: US 12,171,607 B2
(45) Date of Patent: Dec. 24, 2024

(54) IMAGE PROCESSING DEVICE, IMAGE PROCESSING METHOD, AND IMAGE PROCESSING PROGRAM

(71) Applicant: FUJIFILM CORPORATION, Tokyo (JP)

(72) Inventor: Takahiro Kawamura, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 376 days.

(21) Appl. No.: 17/676,815

(22) Filed: Feb. 22, 2022

(65) Prior Publication Data
US 2022/0175333 A1 Jun. 9, 2022

Related U.S. Application Data

(63) Continuation of application No. PCT/JP2020/032749, filed on Aug. 28, 2020.

(30) Foreign Application Priority Data

Sep. 18, 2019 (JP) ................................ 2019-169270
Jul. 30, 2020 (JP) ................................ 2020-129560

(51) Int. Cl.
*A61B 6/50* (2024.01)
*A61B 6/00* (2006.01)
(Continued)

(52) U.S. Cl.
CPC ............ *A61B 6/505* (2013.01); *A61B 6/5205* (2013.01); *G06T 1/0007* (2013.01);
(Continued)

(58) Field of Classification Search
CPC ....... A61B 6/505; A61B 6/5205; A61B 6/482; A61B 6/483; A61B 6/5217; A61B 6/5282;
(Continued)

(56) References Cited

U.S. PATENT DOCUMENTS 10,916,011 B2 * 2/2021 Kawamura .......... A61B 6/5258
2002/0085671 A1   7/2002 Sakaida
(Continued)

FOREIGN PATENT DOCUMENTS

JP    2002-152593 A    5/2002
JP    2018-015453 A    2/2018

OTHER PUBLICATIONS

International Search Report issued in International Application No. PCT/JP2020/032749 on Sep. 29, 2020.
(Continued)

*Primary Examiner* — Dhaval V Patel
(74) *Attorney, Agent, or Firm* — SOLARIS Intellectual Property Group, PLLC (57) ABSTRACT

An image acquisition unit acquires two radiographic images based on radiation which has different energy distributions and has been transmitted through a subject including a soft part and a bone part. An attenuation coefficient derivation unit derives a difference between a value of an attenuation coefficient of the soft part×a thickness of the soft part+an attenuation coefficient of the bone part×a thickness of the bone part and each pixel value of the radiographic image for each of the different energy distributions while changing the attenuation coefficient of the soft part for each of the different energy distributions, the thickness of the soft part, the attenuation coefficient of the bone part for each of the different energy distributions, and the thickness of the bone part from initial values and derives the attenuation coefficient of the soft part and the attenuation coefficient of the bone part for each of the different energy distributions at which the difference is minimized or the difference is less than a predetermined threshold value.

5 Claims, 6 Drawing Sheets

(51) Int. Cl.
*G06T 1/00* (2006.01)
*G06T 7/00* (2017.01)

(52) U.S. Cl.
CPC .. *G06T 7/0012* (2013.01); *G06T 2207/10116* (2013.01); *G06T 2207/30008* (2013.01)

(58) Field of Classification Search
CPC ..... A61B 6/544; G06T 1/0007; G06T 7/0012; G06T 2207/10116; G06T 2207/30008
See application file for complete search history.

(56) References Cited

U.S. PATENT DOCUMENTS

| | | | |
|---|---|---|---|
| 2016/0213344 A1* | 7/2016 | Yi | A61B 6/4241 |
| 2017/0186195 A1* | 6/2017 | Lin | A61B 6/482 |
| 2018/0028139 A1 | 2/2018 | Kuwabara | |
| 2018/0300879 A1* | 10/2018 | Fu | G06T 11/00 |
| 2018/0333121 A1* | 11/2018 | Kuwabara | A61B 6/505 |

OTHER PUBLICATIONS

Written Opinion of the ISA issued in International Application No. PCT/JP2020/032749 on Sep. 29, 2020.

\* cited by examiner

FIG. 7

IMAGE PROCESSING DEVICE, IMAGE PROCESSING METHOD, AND IMAGE PROCESSING PROGRAM

CROSS REFERENCE TO RELATED APPLICATIONS

The present application is a Continuation of PCT International Application No. PCT/JP2020/032749, filed on Aug. 28, 2020, which claims priority to Japanese Patent Application No. 2019-169270, filed on Sep. 18, 2019 and Japanese Patent Application No. 2020-129560, filed on Jul. 30, 2020. Each application above is hereby expressly incorporated by reference, in its entirety, into the present application.

BACKGROUND

Technical Field

The present disclosure relates to an image processing device, an image processing method, and an image processing program.

Related Art

In the related art, an energy subtraction process is known which uses two radiographic images obtained by irradiating a subject with two types of radiation having different energy distributions, using the fact that the amount of attenuation of the transmitted radiation varies depending on a substance constituting the subject. The energy subtraction process is a method which makes pixels of the two radiographic images obtained as described above correspond to each other, multiplies the corresponding pixels by an appropriate weighting coefficient, and performs subtraction to acquire an image obtained by extracting a specific structure. In a case in which the energy subtraction process is performed to derive a soft part image obtained by extracting a soft part from, for example, a radiographic image acquired by imaging the chest, it is possible to observe shadows that appear in the soft part without being disturbed by a bone part. On the contrary, in a case in which a bone part image obtained by extracting a bone part is derived, it is possible to observe shadows that appear in the bone part without being disturbed by the soft part.

In addition, a method has been proposed which acquires bone mineral content used to diagnose a bone-based disease, such as osteoporosis, using a bone part image acquired by the energy subtraction process. For example, JP2018-015453A discloses a radiography apparatus which comprises two radiation detectors that include a plurality of pixels accumulating charge corresponding to the emitted radiation and are disposed to be stacked. Further, a technique is known which measures the bone mineral content of a subject using each electric signal corresponding to the dose of radiation emitted to each radiation detector in this type of radiography apparatus.

However, in a case in which the energy subtraction process is performed, weighting coefficients for two radiographic images acquired by radiation having different energy distributions are derived on the basis of the attenuation coefficients of the soft part and the bone part for the radiation having different energy distributions. Here, the substance has a radiation attenuation coefficient depending on the energy of the radiation. On the other hand, in a case in which the radiation emitted to the subject is not monochromatic, but is distributed in a certain energy range, a so-called beam hardening phenomenon occurs in which the energy distribution of the detected radiation changes depending on the thickness of the substance (a bone part and a soft part in the case of the human body) included in the subject. That is, the attenuation coefficient depends on the energy of the radiation. The attenuation coefficient has the characteristic that, as the energy of a component becomes higher, the attenuation coefficient becomes smaller. Therefore, the radiation loses a relatively large number of low-energy components while passing through the substance, and the proportion of high-energy components increases. This phenomenon is beam hardening. Therefore, in a case in which the weighting coefficient is derived, an attenuation coefficient obtained by weighting the radiation attenuation coefficient of the substance with the detected radiation energy distribution and averaging the weighted radiation attenuation coefficient is used. In addition, the average attenuation coefficient varies depending on the thickness of the substance.

Here, the attenuation coefficient for deriving the weighting coefficient used in a case in which the energy subtraction process is performed is calculated by, for example, presumption on the basis of a low-energy image acquired by low-energy radiation having a low energy distribution. Therefore, in a case in which the energy subtraction process is performed, the same attenuation coefficient is used as the weighting coefficient in all of the pixels. However, the thickness of the substance in the subject varies depending on the location of the subject. Further, as described above, the attenuation coefficient varies depending on the thickness of the substance in the subject. Therefore, for example, in a case in which the subject is a human body, the thickness of the soft part and the bone part is not constant depending on the part. In a case in which the same attenuation coefficient is used as the weighting coefficient in all of the pixels, it is difficult to completely remove an unnecessary structure in a difference image. As a result, there is a problem that the bone part remains in the soft part image and the soft part remains in the bone part image.

Therefore, a method has been proposed which calculates in advance a relationship between a difference between the logarithmic values of radiation doses of pixels in two radiographic images acquired by radiation having different energy distributions or a ratio or difference between the radiation doses of the pixels in the two radiographic images and an attenuation coefficient that is used as a weighting coefficient in a case in which a subtraction process is performed, derives the attenuation coefficient with reference to the relationship, and performs the subtraction process using the derived attenuation coefficient as the weighting coefficient (see JP2002-152593A). The ratio or difference between the radiation doses used in the method described in JP2002-152593A reflects the influence of beam hardening caused by the difference in the thickness of the subject, and the weighting coefficient is calculated according to the degree of beam hardening. Therefore, according to the method described in JP2002-152593A, it is possible to obtain a difference image obtained by appropriately extracting the soft part and the bone part, that is, a soft part image and a bone part image in consideration of the influence of the beam hardening.

However, for the ratio or difference between the radiation doses in the method described in JP2002-152593A, it is not considered that the attenuation characteristics of the radiation vary depending on the composition (the soft part and the bone part) constituting the body of the subject. Therefore, in the method described in JP2002-152593A, the weighting coefficient may not be optimal in a case in which a composition ratio is different. Therefore, even in a case in which the weighting coefficient derived by the method described in JP2002-152593A is used, it is difficult to separate tissues with high accuracy. Therefore, there is a concern that an unnecessary structure will be included in the difference image.

SUMMARY OF THE INVENTION

The present disclosure has been made in view of the above circumstances, and an object of the present disclosure is to provide a technique that can remove an unnecessary structure in a difference image derived by an energy subtraction process with high accuracy.

According to the present disclosure, there is provided an image processing device comprising: an image acquisition unit that acquires two radiographic images based on radiation which has different energy distributions and has been transmitted through a subject including a soft part and a bone part; and an attenuation coefficient derivation unit that derives a difference between a value of an attenuation coefficient of the soft part×a thickness of the soft part+an attenuation coefficient of the bone part×a thickness of the bone part and each pixel value of the radiographic image for each of the different energy distributions while changing the attenuation coefficient of the soft part for each of the different energy distributions, the thickness of the soft part, the attenuation coefficient of the bone part for each of the different energy distributions, and the thickness of the bone part from initial values and derives the attenuation coefficient of the soft part and the attenuation coefficient of the bone part for each of the different energy distributions at which the difference is minimized or the difference is less than a predetermined threshold value.

In addition, the image processing device according to the present disclosure may further comprise a weighting coefficient derivation unit that derives a weighting coefficient for performing a subtraction process, which performs weighting subtraction between corresponding pixels of the two radiographic images to derive a bone part image obtained by extracting the bone part of the subject and a soft part image obtained by extracting the soft part of the subject, on the basis of the attenuation coefficients.

Further, the image processing device according to the present disclosure may further comprise a subtraction unit that performs the weighting subtraction using the weighting coefficient between the corresponding pixels of the two radiographic images to derive the bone part image and the soft part image.

Furthermore, the image processing device according to the present disclosure may further comprise a scattered ray removal unit that removes scattered ray components included in the acquired two radiographic images.

Moreover, in the image processing device according to the present disclosure, the scattered ray removal unit may remove the scattered ray components included in the two radiographic images on the basis of radiation characteristics of an object interposed between the subject and detection units that acquire the two radiographic images.

In addition, in the image processing device according to the present disclosure, two detection units that are superimposed on each other may be irradiated with the radiation transmitted through the subject at the same time to acquire the two radiographic images.

Further, the image processing device according to the present disclosure may further comprise an initial value derivation unit that derives the initial values on the basis of a body thickness of the subject.

Furthermore, the image processing device according to the present disclosure may further comprise a body thickness derivation unit that derives the body thickness of the subject.

According to the present disclosure, there is provided an image processing method comprising: acquiring two radiographic images based on radiation which has different energy distributions and has been transmitted through a subject including a soft part and a bone part; and deriving a difference between a value of an attenuation coefficient of the soft part×a thickness of the soft part+an attenuation coefficient of the bone part×a thickness of the bone part and each pixel value of the radiographic image for each of the different energy distributions while changing the attenuation coefficient of the soft part for each of the different energy distributions, the thickness of the soft part, the attenuation coefficient of the bone part for each of the different energy distributions, and the thickness of the bone part from initial values and deriving the attenuation coefficient of the soft part and the attenuation coefficient of the bone part for each of the different energy distributions at which the difference is minimized or the difference is less than a predetermined threshold value.

In addition, a program that causes a computer to perform the image processing method according to the present disclosure may be provided.

Another image processing device according to the present disclosure comprises a memory that stores commands to be executed by a computer and a processor configured to execute the stored commands. The processor performs a process including: acquiring two radiographic images based on radiation which has different energy distributions and has been transmitted through a subject including a soft part and a bone part; and deriving a difference between a value of an attenuation coefficient of the soft part×a thickness of the soft part+an attenuation coefficient of the bone part×a thickness of the bone part and each pixel value of the radiographic image for each of the different energy distributions while changing the attenuation coefficient of the soft part for each of the different energy distributions, the thickness of the soft part, the attenuation coefficient of the bone part for each of the different energy distributions, and the thickness of the bone part from initial values, and deriving the attenuation coefficient of the soft part and the attenuation coefficient of the bone part for each of the different energy distributions at which the difference is minimized or the difference is less than a predetermined threshold value.

According to the present disclosure, it is possible to remove an unnecessary structure in a derived difference image with high accuracy.

DETAILED DESCRIPTION

Figure 1:
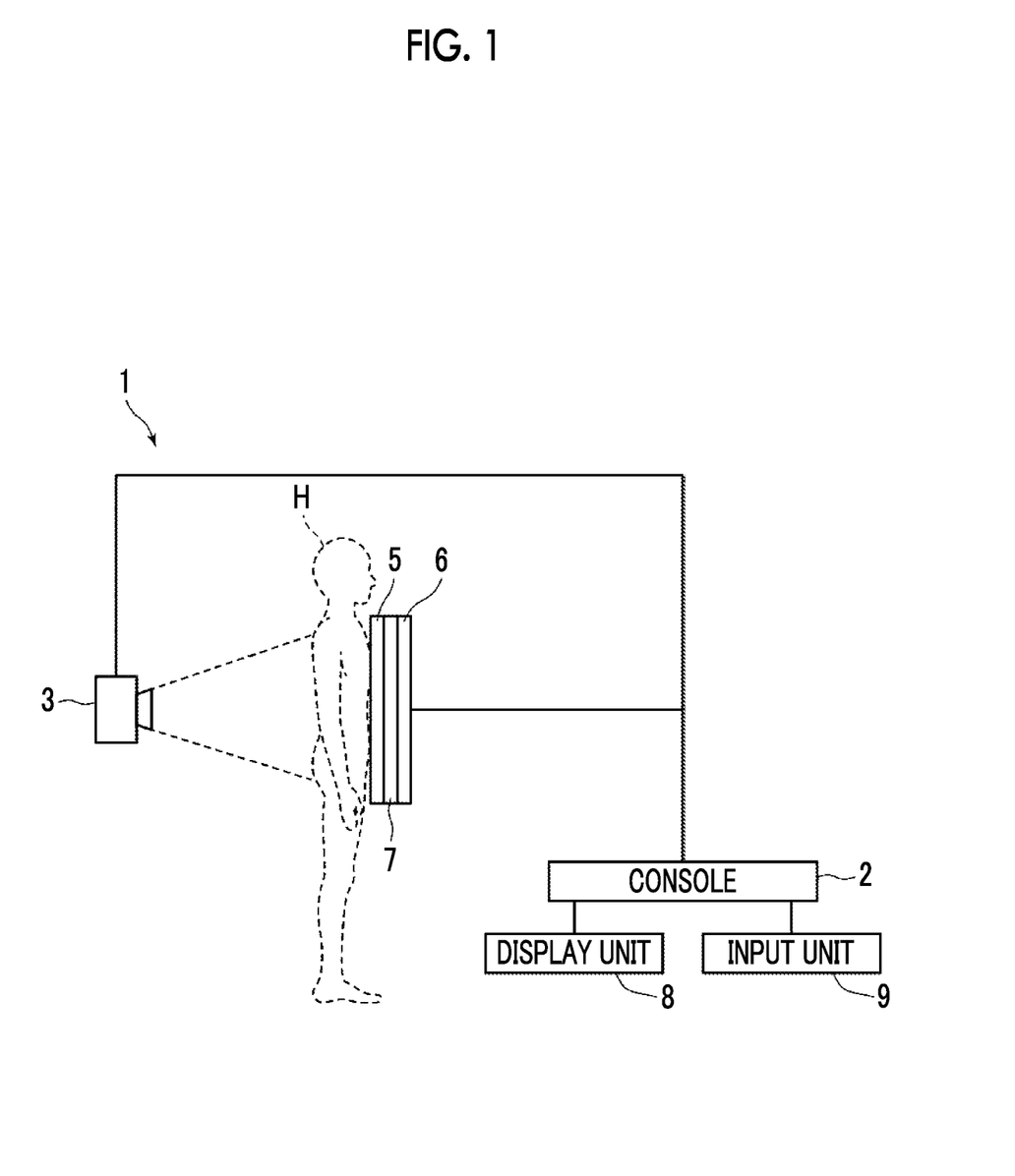
FIG. 1 is a diagram schematically illustrating a configuration of a radiography apparatus to which an image processing device according to an embodiment of the present disclosure is applied.

Hereinafter, embodiments of the present disclosure will be described with reference to the drawings. FIG. 1 is a block diagram schematically illustrating a configuration of a radiography system to which an image processing device according to an embodiment of the present disclosure is applied. As illustrated in FIG. 1, the radiography system according to this embodiment captures two radiographic images having different energy distributions, performs an energy subtraction process using the two radiographic images, and comprises an imaging apparatus 1 and a console 2 including the image processing device according to this embodiment.

The imaging apparatus 1 is an imaging apparatus for performing so-called one-shot energy subtraction that irradiates each of a first radiation detector 5 and a second radiation detector 6 with radiation, such as an X-ray, which has been emitted from a radiation source 3 and transmitted through a subject H, while changing energy. At the time of imaging, as illustrated in FIG. 1, the first radiation detector 5, a radiation energy conversion filter 7 that consists of, for example, a copper plate, and the second radiation detector 6 are disposed in this order from the side closer to the radiation source 3, and the radiation source 3 is driven. In addition, the first and second radiation detectors 5 and 6 and the radiation energy conversion filter 7 are closely attached to each other.

With this configuration, the first radiation detector 5 acquires a first radiographic image G1 of the subject H obtained by low-energy radiation including so-called soft rays. Further, the second radiation detector 6 acquires a second radiographic image G2 of the subject H obtained by high-energy radiation excluding soft rays. The first and second radiographic images are input to the console 2. In addition, in this embodiment, in a case in which the subject H is imaged, a scattered ray removal grid that removes a scattered ray component of the radiation transmitted through the subject H is not used. Therefore, the first radiographic image G1 and the second radiographic image G2 include a primary ray component and a scattered ray component of the radiation transmitted through the subject H.

The first and second radiation detectors 5 and 6 can repeatedly perform the recording and reading of a radiographic image and may be a so-called direct-type radiation detector that directly receives the emitted radiation and generates charge or a so-called indirect-type radiation detector that converts radiation into visible light and then converts the visible light into a charge signal. In addition, as a method for reading a radiographic image signal, it is desirable to use a so-called thin film transistor (TFT) reading method which turns on and off a TFT switch to read out a radiographic image signal or a so-called optical reading method which emits reading light to read out a radiographic image signal. However, the present disclosure is not limited thereto, and other methods may be used.

A display unit 8 and an input unit 9 are connected to the console 2. The display unit 8 consists of a display, such as a cathode ray tube (CRT) or a liquid crystal display, and assists the input of radiographic images acquired by imaging, a soft part image and a bone part image, which will be described below, and various kinds of information necessary for processes performed in the console 2.

The input unit 9 consists of a keyboard, a mouse, or a touch-panel-type input device and receives instructions to operate the imaging apparatus 1 from an operator. In addition, the input unit 9 receives the input of various kinds of information required for imaging, such as imaging conditions, and an instruction to correct information. In this embodiment, each unit of the imaging apparatus 1 is operated according to the information input by the operator through the input unit 9.

An energy subtraction processing program including an image processing program according to this embodiment is installed in the console 2. The console 2 corresponds to an energy subtraction processing device to which the image processing device according to this embodiment is applied. In this embodiment, the console 2 may be a workstation or a personal computer that is directly operated by the operator or a server computer that is connected to them through a network. In addition, the energy subtraction processing program is stored in a storage device of the server computer connected to the network or a network storage in a state in which it can be accessed from the outside and is downloaded and installed in the computer as required. Alternatively, the energy subtraction processing program is recorded on a recording medium, such as a digital versatile disc (DVD) or a compact disc read only memory (CD-ROM), is distributed, and is installed in the computer from the recording medium.

Figure 2:
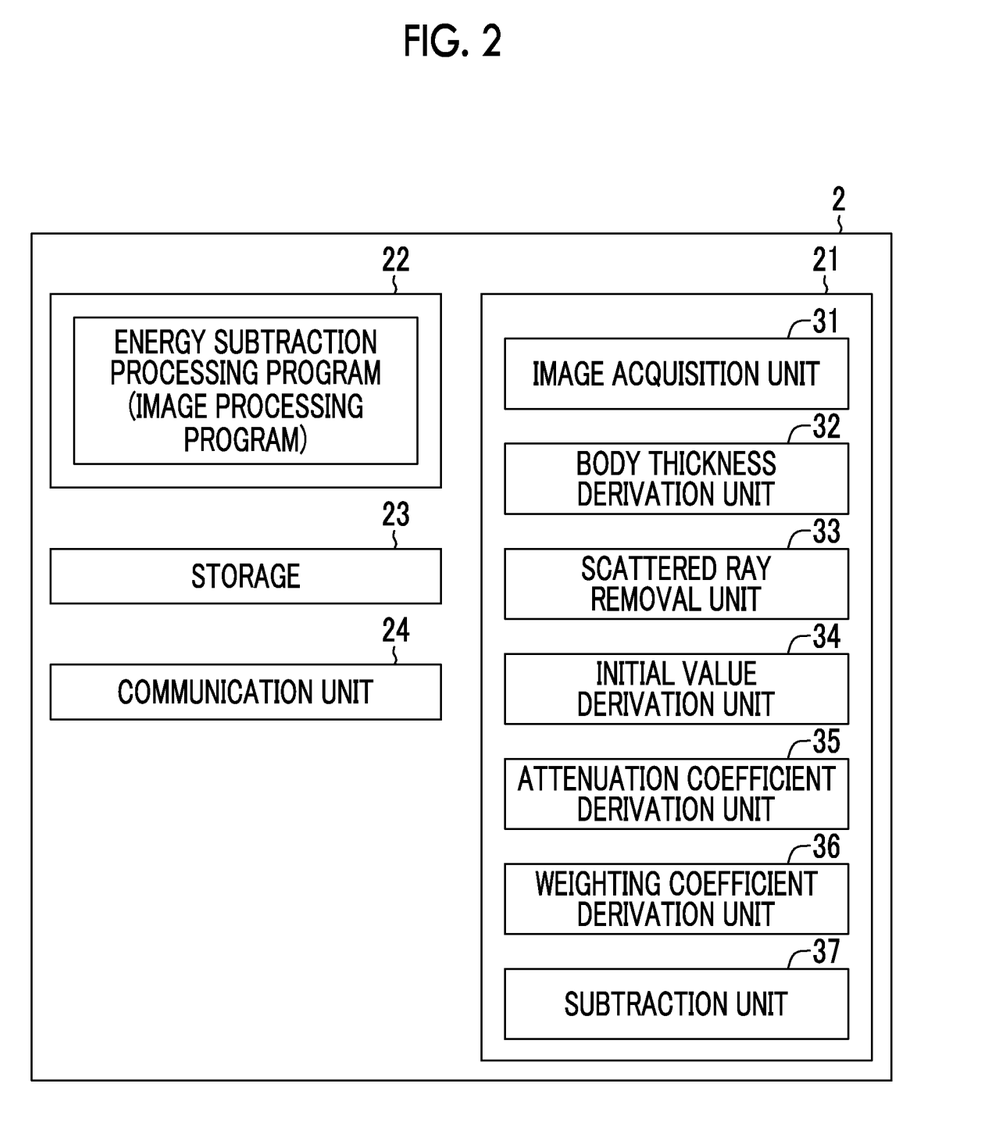
FIG. 2 is a diagram schematically illustrating a configuration of the image processing device according to this embodiment.

FIG. 2 is a diagram illustrating a schematic configuration of the energy subtraction processing device that is implemented by installing the energy subtraction processing program in the computer constituting the console 2 and includes the image processing device according to this embodiment. As illustrated in FIG. 2, the energy subtraction processing device comprises a central processing unit (CPU) 21, a memory 22, a storage 23, and a communication unit 24 as a standard computer configuration.

The storage 23 consists of a storage device, such as a hard disk drive or a solid state drive (SSD), and stores various kinds of information including a program for driving each unit of the imaging apparatus 1 and the energy subtraction processing program. In addition, the radiographic image acquired by imaging is stored in the storage 23.

The communication unit 24 is a network interface that controls the transmission of various kinds of information through the network (not illustrated).

For example, the energy subtraction processing program stored in the storage 23 is temporarily stored in the memory 22 in order to cause the CPU 21 to perform various processes. The energy subtraction processing program defines, as processes performed by the CPU 21, an image acquisition process of directing the imaging apparatus 1 to perform imaging to acquire the first and second radiographic images G1 and G2 having different energy distributions, a body thickness derivation process of deriving the body thickness of the subject H, a scattered ray removal process of removing scattered ray components included in the first and second radiographic images G1 and G2, an initial value derivation process of deriving initial values of an attenuation coefficient of a soft part for each of the different energy distributions, a thickness of the soft part, an attenuation coefficient of a bone part for each of the different energy distributions, and a thickness of the bone part which are used to derive a weighting coefficient in a case in which an energy subtraction process, which will be described below, is performed, an attenuation coefficient derivation process of deriving the attenuation coefficient of the soft part and the attenuation coefficient of the bone part for each of the different energy distributions, at which a difference between a value of the attenuation coefficient of the soft part×the thickness of the soft part+the attenuation coefficient of the bone part×the thickness of the bone part and each pixel value of the radiographic image is minimized or the difference is less than a predetermined threshold value for each of the different energy distributions, while changing the initial values, a weighting coefficient derivation process of deriving the weighting coefficient for performing the subtraction process on the basis of the derived attenuation coefficients, and the subtraction process of performing weighting subtraction using the weighting coefficient between the corresponding pixels of the first and second radiographic images G1 and G2 to derive a bone part image obtained by extracting the bone part of the subject H and a soft part image obtained by extracting the soft part of the subject H.

Then, the CPU 21 performs these processes such that the energy subtraction processing program such that the console 2 functions as an image acquisition unit 31, a body thickness derivation unit 32, a scattered ray removal unit 33, an initial value derivation unit 34, an attenuation coefficient derivation unit 35, a weighting coefficient derivation unit 36, and a subtraction unit 37.

The image acquisition unit 31 drives the radiation source 3 to irradiate the subject H with radiation, detects the radiation transmitted through the subject H using the first and second radiation detectors 5 and 6, and acquires the first and second radiographic images G1 and G2. In this case, imaging conditions, such as an imaging dose, an energy distribution, a tube voltage, and a SID, are set. The imaging conditions may be set by an input operation of the operator through the input unit 9. The set imaging conditions are stored in the storage 23. In addition, the first and second radiographic images G1 and G2 may be acquired by a program different from the energy subtraction processing program and then stored in the storage 23. In this case, the image acquisition unit 31 reads out the first and second radiographic images G1 and G2 stored in the storage 23 from the storage 23 in order to process the first and second radiographic images G1 and G2. Further, in this embodiment, it is assumed that the subject H is imaged from the chest to the abdomen and the first and second radiographic images G1 and G2 from the chest to the abdomen are acquired.

The body thickness derivation unit 32 derives the body thickness of the subject H for each pixel of the first and second radiographic images G1 and G2 on the basis of at least one of the first radiographic image G1 or the second radiographic image G2. Since the body thickness is derived for each pixel of the first and second radiographic images G1 and G2, the body thickness derivation unit 32 derives a body thickness distribution in at least one of the first radiographic image G1 or the second radiographic image G2. In a case in which the body thickness is derived, the body thickness derivation unit 32 uses the first radiographic image G1 acquired by the radiation detector 5 closer to the subject H. However, the second radiographic image G2 may be used. Further, even in a case in which any one of the images is used, a low-frequency image indicating a low-frequency component of the image may be derived, and the body thickness may be derived using the low-frequency image.

In this embodiment, assuming that a brightness distribution in the first radiographic image G1 is matched with the distribution of the body thickness of the subject H, the body thickness derivation unit 32 converts the pixel value of the first radiographic image G1 into a thickness using an attenuation coefficient in the soft part of the subject H to derive the body thickness of the subject H. Instead of this, the body thickness derivation unit 32 may measure the body thickness of the subject H using, for example, a sensor. In addition, the body thickness derivation unit 32 may approximate the body thickness of the subject H with a model, such as a cube or an elliptical column, to derive the body thickness. Further, the body thickness derivation unit 32 may derive the body thickness of the subject H using any method such as the method described in, for example, JP2015-043959A.

The scattered ray removal unit 33 removes the scattered ray components which are generated by the scattering of the radiation in the subject and are included in the first and second radiographic images G1 and G2. As a method for removing the scattered ray components, for example, any methods described in JP2014-207958A, JP2015-043959A, and the like can be used. The method described in JP2014-207958A acquires the characteristics of a grid that is assumed to be used to remove scattered rays in a case in which a radiographic image is captured, derives scattered ray components included in the radiographic image on the basis of the characteristics, and performs a scattered ray removal process using the derived scattered ray components. The method described in JP2015-043959A derives scattered ray components using the derived body thickness and performs a scattered ray removal process on the radiographic image. In addition, in the following description, it is assumed that G1 and G2 are used as reference numerals for the first and second radiographic images from which the scattered ray components have been removed, respectively.

Here, the removal of scattered rays in a case in which the method described in JP2015-043959A is used will be described. In a case in which, for example, the method described in JP2015-043959A is used, the derivation of the body thickness and the derivation of scattered ray components for removing scattered rays, which will be described below, are performed at the same time. Therefore, the derivation of the body thickness and the removal of the scattered rays are performed in the body thickness derivation unit 32 and the scattered ray removal unit 33 as follows. First, the body thickness derivation unit 32 and the scattered ray removal unit 33 acquire a virtual model of the subject H having an initial body thickness distribution and derive an estimated primary ray image which is obtained by estimating a primary ray image obtained by imaging the virtual model and an estimated scattered ray image which is obtained by estimating a scattered ray image obtained by imaging the virtual model. Further, in this embodiment, it is assumed that the estimated primary ray image and the estimated scattered ray image are derived using the first radiographic image G1. Then, the body thickness derivation unit 32 and the scattered ray removal unit 33 add the estimated primary ray image and the estimated scattered ray image to derive an estimated image. Furthermore, the body thickness derivation unit 32 and the scattered ray removal unit 33 correct the initial body thickness distribution such that a difference between the estimated image and the first radiographic image G1 is reduced.

Then, the body thickness derivation unit 32 and the scattered ray removal unit 33 derive an estimated image using the corrected body thickness distribution and repeat the generation of the estimated image using the corrected body thickness distribution and the correction of the body thickness distribution until the difference between the estimated image and the first radiographic image G1 satisfies a predetermined end condition. The body thickness derivation unit 32 derives, as the body thickness of the subject H, the body thickness distribution in a case in which the end condition is satisfied. The scattered ray removal unit 33 subtracts the estimated scattered ray image in a case in which the end condition is satisfied from the first radiographic image G1 to remove the scattered ray components from the first radiographic image G1. In addition, the scattered ray removal unit 33 derives an estimated scattered ray image for the second radiographic image G2 using the same method as that for the first radiographic image G1 and subtracts the derived estimated scattered ray image from the second radiographic image G2 to remove the scattered ray components from the second radiographic image G2.

The initial value derivation unit 34 derives the initial values of the attenuation coefficient of the soft part for each of the different energy distributions, the thickness of the soft part, the attenuation coefficient of the bone part for each of the different energy distributions, and the thickness of the bone part which are used to derive the weighting coefficient in a case in which the energy subtraction process is performed. Specifically, initial values $\mu$ls0, $\mu$hs0, ts0, $\mu$lb0, $\mu$hb0, and tb0 of an attenuation coefficient $\mu$ls of the soft part for low-energy radiation, an attenuation coefficient $\mu$hs of the soft part for high-energy radiation, a thickness ts of the soft part, an attenuation coefficient $\mu$lb of the bone part for low-energy radiation, an attenuation coefficient $\mu$hb of the bone part for high-energy radiation, and a thickness tb of the bone part are derived.

Here, in this embodiment, the subtraction unit 37 performs the subtraction process of performing weighting subtraction between the corresponding pixels of the first and second radiographic images G1 and G2, using the weighting coefficient derived by the weighting coefficient derivation unit 36 as described below, to derive a soft part image Gs obtained by extracting the soft part of the subject H and a bone part image Gb obtained by extracting the bone part of the subject H, as represented by the following Expressions (1) and (2). In Expressions (1) and (2), $\alpha$ and $\beta$ are weighting coefficients.

$$Gs(x,y) = \alpha \cdot G2(x,y) - G1(x,y) \quad (1)$$

$$Gb(x,y) = \beta \cdot G2(x,y) - G1(x,y) \quad (2)$$

Here, the relationship between the weighting coefficients $\alpha$ and $\beta$ and a radiation attenuation coefficient will be described. Here, the radiation emitted from the radiation source 3 has an energy distribution. The attenuation coefficient also depends on the energy of the radiation. The radiation has the characteristic that, as the energy of a component becomes higher, the attenuation coefficient becomes smaller. Therefore, a so-called beam hardening phenomenon occurs in which radiation loses a relatively large number of low-energy components while passing through a substance and the proportion of high-energy components increases. Since the degree of beam hardening depends on a thickness ts of the soft part and a thickness tb of the bone part in the subject H, an attenuation coefficient $\mu$s of the soft part and an attenuation coefficient $\mu$b of the bone part can be defined as $\mu$s(ts, tb) and $\mu$b(ts, tb) as functions of ts and tb, respectively.

In the energy subtraction process, there are images having two different energy distributions. Therefore, in the low-energy image (the first radiographic image G1 in this embodiment), the attenuation coefficient of the soft part can be represented by $\mu$ls(ts, tb), and the attenuation coefficient of the bone part can be represented by $\mu$lb(ts, tb). Further, in the high-energy image (the second radiographic image G2 in this embodiment), the attenuation coefficient of the soft part can be represented by $\mu$hs(ts, tb), and the attenuation coefficient of the bone part can be represented by $\mu$hb(ts, tb).

It is necessary to eliminate the contrast of the bone part included in the radiographic image in order to derive the soft part image Gs. Therefore, the weighting coefficient $\alpha$ can be calculated by $\alpha = \mu$lb(ts, tb)/$\mu$hb(ts, tb) using the ratio of the attenuation coefficients of the bone part. Further, it is necessary to eliminate the contrast of the soft part included in the radiographic image in order to derive the bone part image Gb. Therefore, the weighting coefficient $\beta$ can be calculated by $\beta = \mu$ls(ts, tb)/$\mu$hs(ts, tb) using the ratio of the attenuation coefficients of the soft part. In addition, in the following description, the attenuation coefficients $\mu$ls(ts, tb), $\mu$hs(ts, tb), $\mu$lb(ts, tb), and $\mu$hb(ts, tb) are simply expressed as attenuation coefficients $\mu$ls, $\mu$hs, $\mu$lb, and $\mu$hb, respectively, by omitting (ts, tb).

The initial value derivation unit 34 uses the body thickness estimated by the body thickness derivation unit 32 as the initial value ts0 of the thickness ts of the soft part. Since the body thickness derivation unit 32 sets the initial value tb0 of the thickness tb of the bone part to 0 since the body thickness is used assuming that the subject H consists of only the soft part. In addition, as the initial values $\mu$ls0, $\mu$hs0, $\mu$lb0, and $\mu$hb0 of the attenuation coefficients, values corresponding to the initial values ts0 and tb0 of the thicknesses ts and tb of the soft part and the bone part are derived. In this embodiment, since the initial value tb0 of the thickness tb of the bone part is 0, the attenuation coefficients $\mu$lb0 and $\mu$hb0 of the bone part are 0. As the attenuation coefficients $\mu$ls0 and $\mu$hs0 of the soft part, values corresponding to the initial value ts0 of the thickness ts of the soft part are derived. Therefore, in this embodiment, a table that defines the relationship between the initial value ts0 of the thickness ts of the soft part and the initial values $\mu$ls0 and $\mu$hs0 of the attenuation coefficients of the soft part is stored in the storage 23.

Figure 3:
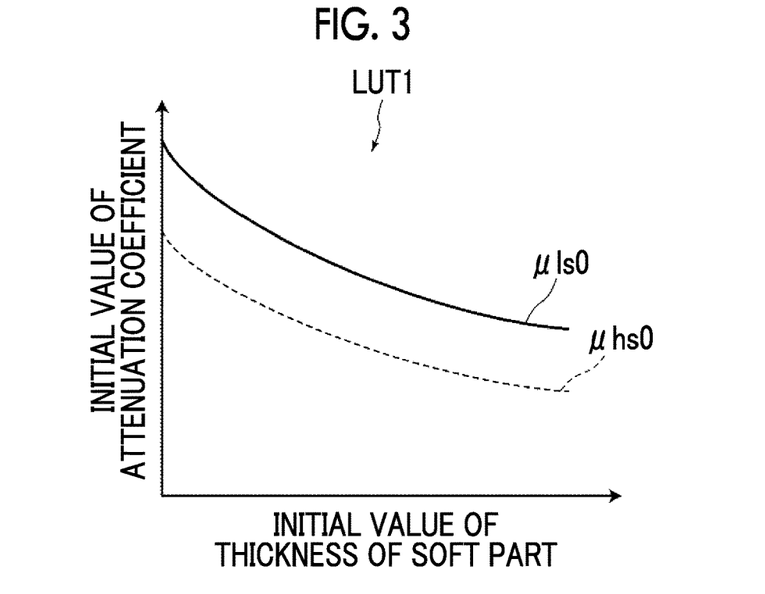
FIG. 3 is a diagram illustrating a table that defines a relationship between an initial value of a thickness of a soft part and an attenuation coefficient.

FIG. 3 is a diagram illustrating the table that defines the relationship between the initial value ts0 of the thickness ts of the soft part and the initial values $\mu$ls0 and $\mu$hs0 of the attenuation coefficients of the soft part. The initial value derivation unit 34 derives the initial values $\mu$ls0 and $\mu$hs0 of the attenuation coefficients of the soft part corresponding to the initial value ts0 of the thickness ts of the soft part with reference to a table LUT1 stored in the storage 23.

The attenuation coefficient derivation unit 35 derives the attenuation coefficients $\mu$ls and $\mu$hs of the soft part and the attenuation coefficients $\mu$lb and $\mu$hb of the bone part for different energy distributions. Here, the subject H is imaged with radiation having different energy distributions to acquire a low-energy image and a high-energy image for the energy subtraction process. In this embodiment, the first radiographic image G1 is a low-energy image, and the second radiographic image G2 is a high-energy image. In addition, a pixel value G1(x, y) of each pixel of the first radiographic image G1 which is the low-energy image and a pixel value G2(x, y) of each pixel of the second radiographic image G2 which is the high-energy image are represented by the following Expressions (3) and (4) using the thickness ts(x, y) of the soft part, the thickness tb(x, y) of the bone part, and the attenuation coefficients $\mu$ls(x, y), μhs(x, y), μlb(x,y), and μhb(x, y) at the corresponding pixel position, respectively. In addition, in Expressions (3) and (4), (x, y) is omitted.

$$G1 = \mu sl \times ts + \mu bl \times tb \quad (3)$$

$$G2 = \mu sh \times ts + \mu bh \times tb \quad (4)$$

It is necessary to derive the attenuation coefficients μls(x, y), μhs(x, y), μlb(x, y), and μhb(x, y) in order to derive the weighting coefficients α and β for performing the energy subtraction process. The attenuation coefficients μls(x, y), μhs(x, y), μlb(x, y), and μhb(x, y) are expressed as functions of the thickness ts of the soft part and the thickness tb of the bone part as described above. Therefore, it is necessary to derive the thickness ts of the soft part and the thickness tb of the bone part in order to derive the attenuation coefficients μls(x, y), μhs(x, y), μlb(x, y), and μhb(x, y). In a case in which Expressions (3) and (4) are solved for ts and tb, the following Expressions (5) and (6) are obtained.

$$ts = \{\mu hb \times G1 - \mu lb \times G2\}/\{\mu ls \times \mu hb - \mu lb \times \mu hs\} \quad (5)$$

$$tb = \{\mu ls \times G2 - \mu hs \times G1\}/\{\mu ls \times \mu hb - \mu lb \times \mu hs\} \quad (6)$$

Here, since the attenuation coefficients μls(x, y), μhs(x, y), μlb(x, y), and μhb(x, y) on the right side of Expressions (5) and (6) are expressed as the functions of the thickness ts of the soft part and the thickness tb of the bone part, it is difficult to algebraically solve Expressions (5) and (6).

Therefore, in this embodiment, error functions EL and EH represented by the following Expressions (7) and (8) are set. The error functions EL and EH correspond to the difference between the value of the attenuation coefficient of the soft part×the thickness of the soft part+the attenuation coefficient of the bone part×the thickness of the bone part and each pixel value of the radiographic image for each of the different energy distributions. Then, in this embodiment, an error function E0 represented by Expression (9) is set in order to minimize the error functions EL and EH at the same time. Then, a combination of the thickness ts of the soft part and the thickness tb of the bone part where the error function E0 is minimized or the error function E0 is less than a predetermined threshold value Th1 is derived while the thickness ts of the soft part, the thickness tb of the bone part, and the attenuation coefficients μls, μhs, μlb, and μhb are changed from the initial values. In this case, it is preferable to derive the thickness ts of the soft part and the thickness tb of the bone part, using optimization algorithms such as a steepest descent method and a conjugate gradient method. The initial values of the thickness ts of the soft part, the thickness tb of the bone part, and the attenuation coefficients μls, μhs, μlb, and μhb used at this time are ts0, tb0, μls0, μhs0, μlb0, and μhb0 derived by the initial value derivation unit 34, respectively.

$$EL = G1 - \{\mu sl \times ts + \mu bl \times tb\} \quad (7)$$

$$EH = G2 - \{\mu sh \times ts + \mu bh \times tb\} \quad (8)$$

$$E0 = EL^2 + EH^2 \quad (9)$$

Figure 4:
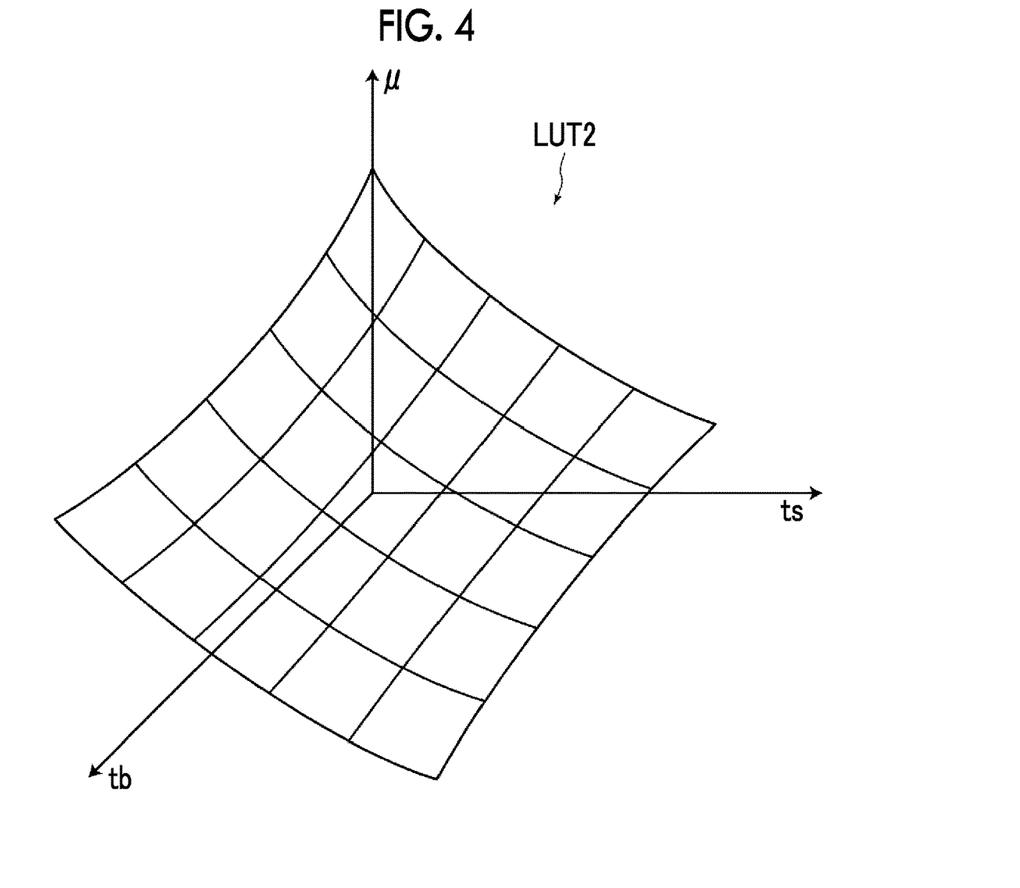
FIG. 4 is a diagram illustrating a table that defines a relationship among the thickness of the soft part, a thickness of a bone part, and an attenuation coefficient.

In addition, the attenuation coefficients used in the process of deriving the thickness ts of the soft part and the thickness tb of the bone part are derived with reference to a table that defines the relationship among the predetermined thickness ts of the soft part, the predetermined thickness tb of the bone part, and the attenuation coefficients. The table is stored in the storage 23. FIG. 4 is a diagram illustrating the table defining the relationship among the thickness ts of the soft part, the thickness tb of the bone part, and the attenuation coefficient. As illustrated in FIG. 4, a table LUT2 three-dimensionally represents the relationship among the thickness ts of the soft part, the thickness tb of the bone part, and the attenuation coefficient μ. In addition, only one LUT2 is illustrated in FIG. 4. However, the tables are prepared for each of the attenuation coefficients μls, μhs, μlb, and μhb and stored in the storage 23. Here, in the table LUT2, as the thickness ts of the soft part and the thickness tb of the bone part become larger, the attenuation coefficient μ becomes smaller.

In a case in which the thickness ts of the soft part and the thickness tb of the bone part that minimize the error function E0 are derived, the attenuation coefficient derivation unit 35 derives the attenuation coefficients μls, μhs, μlb, and μhb with reference to the table LUT2.

The weighting coefficient derivation unit 36 derives the weighting coefficients α and β used in a case in which the subtraction unit 37 performs the subtraction process. That is, the weighting coefficient derivation unit 36 performs the operation of α=μlb/μhb and β=μls/μhs using the attenuation coefficients μls, μhs, μlb, and μhb derived by the attenuation coefficient derivation unit 35 to derive the weighting coefficients α and β.

Figure 5:
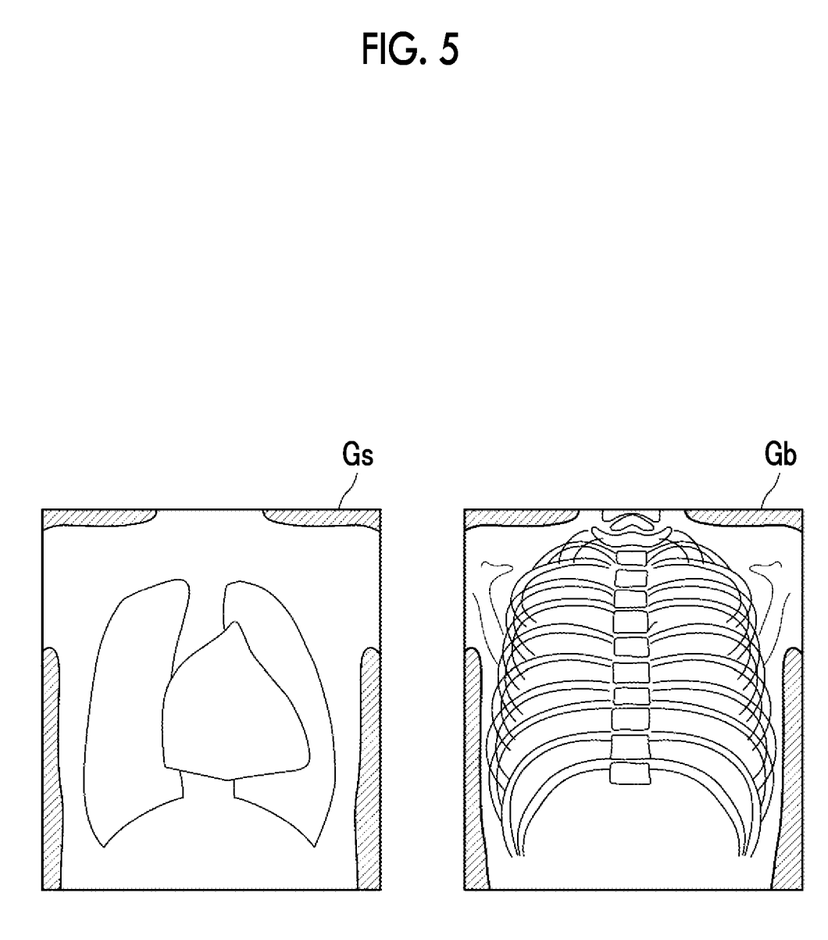
FIG. 5 is a diagram illustrating a soft part image and a bone part image.

The subtraction unit 37 derives the soft part image Gs and the bone part image Gb on the basis of the weighting coefficients α and β derived by the weighting coefficient derivation unit 36, using the above-described Expressions (1) and (2). FIG. 5 is a diagram illustrating the soft part image Gs and the bone part image Gb. As illustrated in FIG. 5, the soft part image Gs is obtained by extracting the soft part of the subject H. Further, the bone part image Gb is obtained by extracting the bone part of the subject H.

Figure 6:
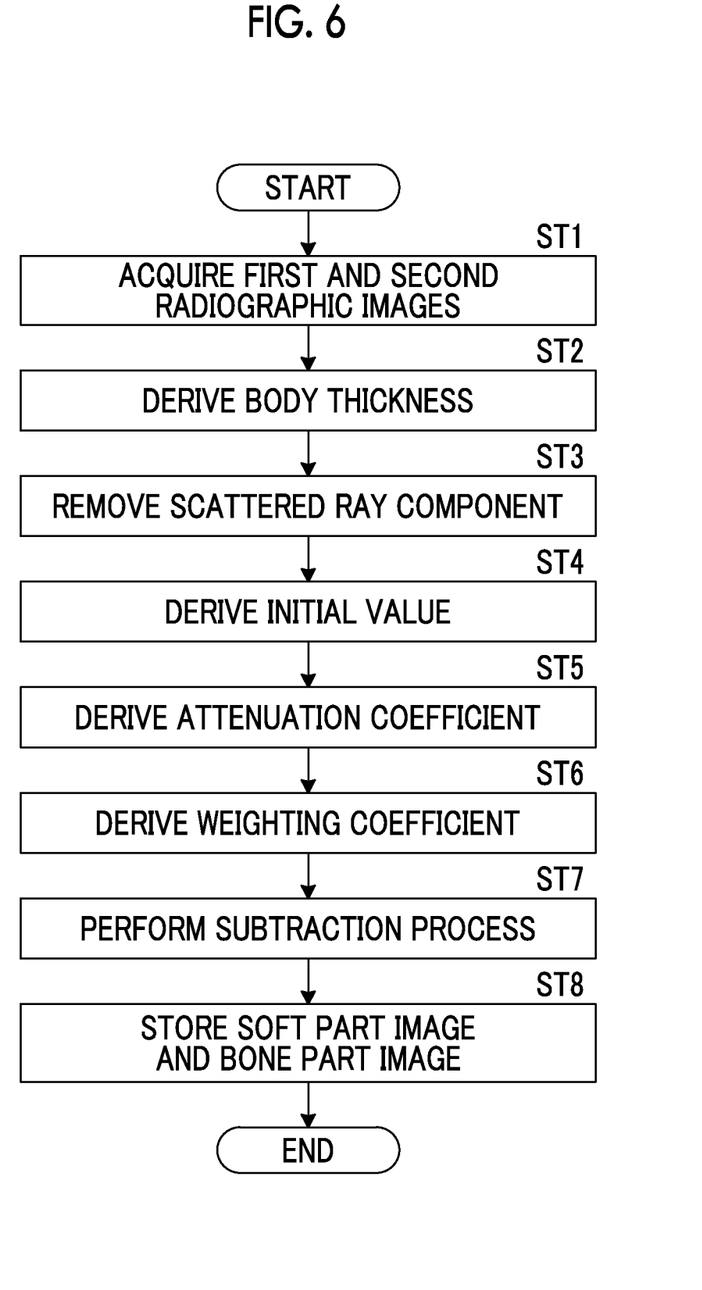
FIG. 6 is a flowchart illustrating a process performed in this embodiment.

Next, a process performed in this embodiment will be described. FIG. 6 is a flowchart illustrating the process performed in this embodiment. In addition, it is assumed that the first and second radiographic images G1 and G2 are acquired by imaging and are then stored in the storage 23. In a case in which an instruction to start the process is input from the input unit 9, the image acquisition unit 31 acquires the first and second radiographic images G1 and G2 from the storage 23 (Step ST1). Then, the body thickness derivation unit 32 derives the body thickness of the subject H (Step ST2), and the scattered ray removal unit 33 removes the scattered ray components from the first and second radiographic images G1 and G2 (Step ST3).

Then, the initial value derivation unit 34 derives the initial values ts0, tb0, μls0, μhs0, μlb0, and μhb0 of the thickness ts of the soft part, the thickness tb of the bone part, and the attenuation coefficients (the derivation of the initial values; Step ST4). Then, the attenuation coefficient derivation unit 35 derives the thickness ts of the soft part and the thickness tb of the bone part to derive the attenuation coefficients μls, μhs, μlb, and μhb (Step ST5). In addition, the weighting coefficient derivation unit 36 derives the weighting coefficients α and β used in a case in which the subtraction unit 37 performs the subtraction process (Step ST6). Then, the subtraction unit 37 performs the subtraction process on the basis of the weighting coefficients α and β, using the above-described Expressions (1) and (2) (Step ST7). The soft part image Gs and the bone part image Gb are derived by this process. Then, the subtraction unit 37 stores the soft part image Gs and the bone part image Gb in the storage 23 (Step ST8). Then, the process ends. In addition, instead of or in addition to storing the soft part image Gs and the bone part image Gb, the soft part image Gs and the bone part image Gb may be displayed on the display unit 8.

Here, the composition of the human body includes a soft part and a bone part. In the bone part, the attenuation of radiation is greater than that in the soft part, and the radiation transmitted through the bone part shifts to the high energy side. Therefore, it is desirable to derive the weighting coefficients α and β in consideration of bone mass in the subject H in order to accurately separate the soft part and the bone part using the subtraction process.

According to this embodiment, the attenuation coefficient of the soft part and the attenuation coefficient of the bone part for each of different energy distributions, at which the difference between the value of the attenuation coefficient of the soft part×the thickness of the soft part+the attenuation coefficient of the bone part× the thickness of the bone part and each pixel value of the radiographic image is minimized or the difference is less than the predetermined threshold value for each of the different energy distributions, are derived while the attenuation coefficient of the soft part for each of the different energy distributions, the thickness of the soft part, the attenuation coefficient of the bone part for each of the different energy distributions, and the thickness of the bone part are changed from the initial values. Specifically, the thicknesses of the soft part and the bone part and the attenuation coefficients are derived such that the error function E0 in the above-described Expression (9) is minimized or is less than the threshold value Th1. Therefore, according to this embodiment, it is possible to derive the attenuation coefficients in which not only the thickness of the soft part but also the thickness of the bone part has been reflected. Therefore, according to this embodiment, the weighting coefficients for performing the subtraction process are derived from the derived attenuation coefficients, and the weighting subtraction process is performed on the basis of the derived weighting coefficients to remove unnecessary structures in the derived soft part image Gs and bone part image Gb with higher accuracy.

In addition, in the above-described embodiment, the body thickness derivation unit 32 derives the body thickness of the subject H. However, the present disclosure is not limited thereto. The body thickness may not be derived, but a predetermined average body thickness may be used. In this case, the initial value derivation unit 34 derives the initial values of the thickness is of the soft part and the attenuation coefficients using the average body thickness.

Further, in the above-described embodiment, the scattered ray removal unit 33 removes the scattered ray components from the first and second radiographic images G1 and G2. However, the present disclosure is not limited thereto. For example, in a case in which the scattered ray removal filter is used at the time of imaging, the subtraction process and the weighting coefficient derivation process may be performed without removing the scattered ray components from the first and second radiographic images G1 and G2.

Further, in the above-described embodiment, the first and second radiographic images G1 and G2 are acquired by the one-shot method. However, the first and second radiographic images G1 and G2 may be acquired by a so-called two-shot method that performs imaging twice. Further, in the case of the two-shot method, the positions of the subject H included in the first and second radiographic images G1 and G2 are likely to deviate from each other due to the body movement of the subject H. Therefore, it is preferable to perform the process according to this embodiment after registering the positions of the subject in the first and second radiographic images G1 and G2. For example, the method disclosed in JP2011-255060A can be used as the registration process. For example, the method disclosed in JP2011-255060A generates a plurality of first band images and a plurality of second band images indicating structures having different frequency bands for each of first and second radiographic images G1 and G2, acquires the amount of positional deviation between the corresponding positions in the first band image and the second band image of the corresponding frequency band, and registers the first radiographic image G1 and the second radiographic image G2 on the basis of the amount of positional deviation.

Further, in the above-described embodiment, the energy subtraction process is performed using the radiographic images acquired in the system that captures the radiographic images of the subject using the first and second radiation detectors 5 and 6. However, the present disclosure may also be applied to a case in which the first and second radiographic images G1 and G2 are acquired using a storage phosphor sheet as the radiation detector. In this case, the first and second radiographic images G1 and G2 may be acquired by stacking two storage phosphor sheets, irradiating the storage phosphor sheets with radiation transmitted through the subject H such that the radiographic image information of the subject H is accumulated and recorded on each storage phosphor sheet, and photoelectrically reading the radiographic image information from each storage phosphor sheet. In addition, the two-shot method may also be used in a case in which the first and second radiographic images G1 and G2 are acquired using the storage phosphor sheets.

Figure 7:
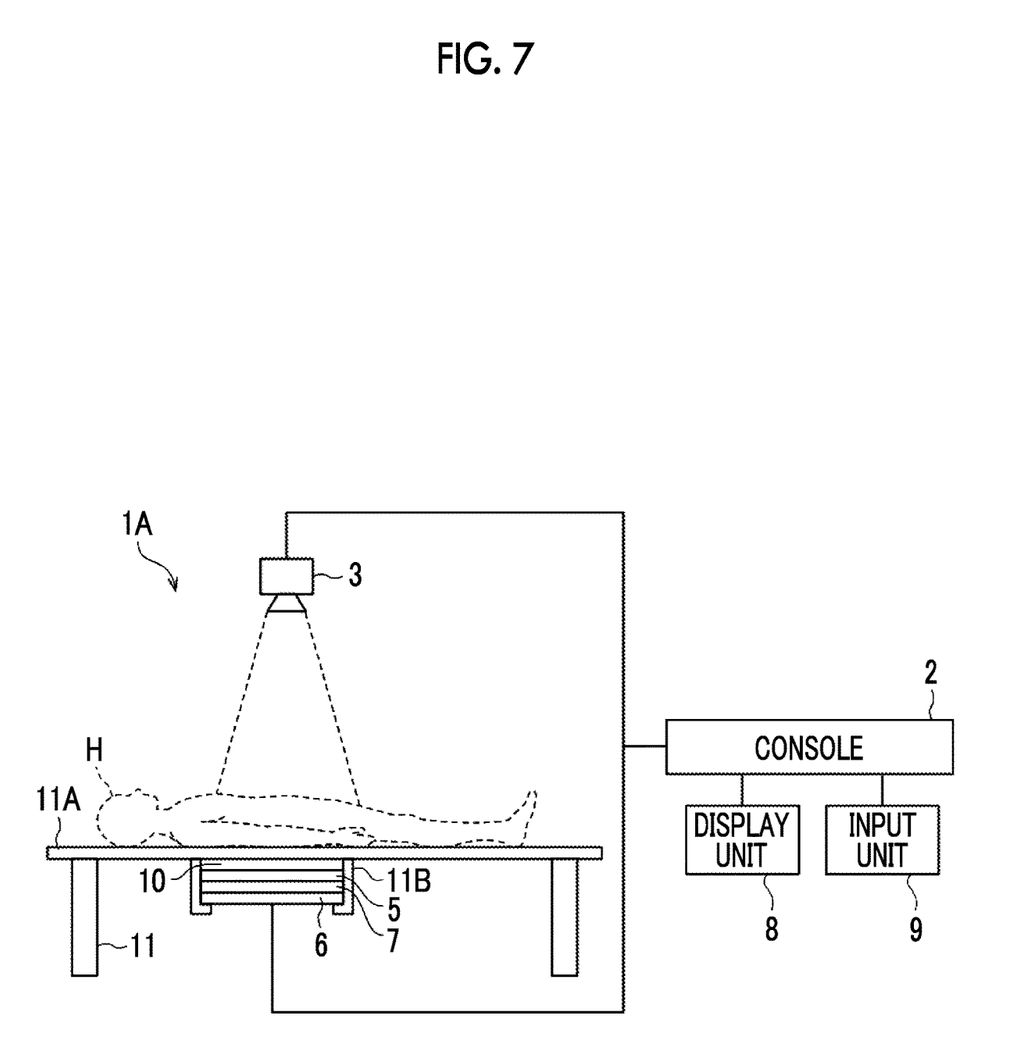
FIG. 7 is a diagram schematically illustrating a configuration of a radiography system to which an image processing device according to another embodiment of the present disclosure is applied.

Furthermore, in the above-described embodiment, the image of the subject H in an upright position is captured. However, as illustrated in FIG. 7, the image of the subject H in a decubitus position may be captured. An imaging apparatus 1A in a radiography system illustrated in FIG. 7 is an imaging apparatus for acquiring a radiographic image of the subject H who lies on an imaging table 11 in a supine position. In the imaging apparatus 1A illustrated in FIG. 7, the first radiation detector 5, the radiation energy conversion filter 7, and the second radiation detector 6 are disposed in this order from the side closer to the radiation source 3. Further, a scattered ray removal grid 10 (hereinafter, simply referred to as a grid) for removing the scattered ray component scattered by the subject H in the radiation transmitted through the subject H is disposed between a top plate 11A of the imaging table 11 and the first radiation detector 5. The grid 10, the first radiation detector 5, the radiation energy conversion filter 7, and the second radiation detector 6 are attachably and detachably attached to the imaging table 11 by an attachment portion 11B that is provided on a lower surface of the top plate 11A of the imaging table 11.

In a case in which the imaging apparatus 1A illustrated in FIG. 7 is used, the top plate 11A of the imaging table 11 and the grid 10 are interposed between the subject H and the first radiation detector 5. In addition, in the imaging apparatus 1 illustrated in FIG. 1 and the imaging apparatus 1A illustrated in FIG. 7, in some cases, air is interposed between the subject H and the first radiation detector 5 at the time of imaging. In this case, the first radiation detector 5 is irradiated with the radiation transmitted through the subject H, the top plate 11A, the grid 10, and an air layer in this order. Here, objects, such as the top plate 11A, the grid 10, and air, have unique radiation characteristics. Therefore, since the radiation is transmitted through the objects, the quality of the primary ray component and the scattered ray component transmitted through the subject H changes depending on the radiation characteristics of the objects. In addition, even in a case in which the grid 10 is used, it is difficult to completely remove the scattered rays. Therefore, the radiation transmitted through the subject H includes a scattered ray component. For this reason, in this embodiment, it is preferable to consider the radiation characteristics of the objects interposed between the subject H and the first radiation detector 5 in a case in which the estimation of the body thickness distribution using the first radiographic image G1 and the removal of the scattered ray component are performed.

Specifically, the primary ray transmittance and the scattered ray transmittance of radiation corresponding to the types of objects interposed between the subject H and the first radiation detector 5 are generated as, for example, a table in advance according to various imaging conditions and the body thickness distribution of the subject H and are stored in the storage 23. Then, in a case in which the body thickness derivation unit 32 and the scattered ray removal unit 33 perform the estimation of the body thickness distribution of the subject H and the removal of the scattered rays, the radiation characteristics of the objects corresponding to the body thickness distribution, that is, the primary ray transmittance and the scattered ray transmittance of radiation are acquired with reference to the table. In addition, the scattered ray removal unit 33 acquires an estimated primary ray image and an estimated scattered ray image, using the acquired radiation characteristics, imaging conditions, and body thickness distribution and adds the estimated primary ray image and the estimated scattered ray image to generate an estimated image. Further, the body thickness derivation unit 32 and the scattered ray removal unit 33 repeatedly perform the generation of the estimated image and the correction of the body thickness distribution until the difference between the estimated image and the first radiographic image G1 satisfies a predetermined end condition. Then, the body thickness derivation unit 32 derives, as the body thickness of the subject H, a body thickness distribution in a case in which the end condition is satisfied. Furthermore, the scattered ray removal unit 33 subtracts the estimated scattered ray image in a case in which the body thickness distribution satisfying the end condition is acquired from the first radiographic image G1 to remove the scattered ray components from the first radiographic image G1. Therefore, it is possible to remove the scattered ray components from the first radiographic image G1 in consideration of the radiation characteristics of the objects interposed between the subject H and the first radiation detector. In addition, similarly, it is possible to remove the scattered ray components from the second radiographic image G2.

Further, the radiation in the above-described embodiment is not particularly limited. For example, α-rays or γ-rays can be applied in addition to the X-rays.

Furthermore, in the above-described embodiment, for example, the following various processors can be used as a hardware structure of processing units performing various processes, such as the image acquisition unit 31, the body thickness derivation unit 32, the scattered ray removal unit 33, the initial value derivation unit 34, the attenuation coefficient derivation unit 35, the weighting coefficient derivation unit 36, and the subtraction unit 37 of the console 2 which is the energy subtraction processing device. The various processors include, for example, a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system on chip (SoC). As such, various processing units are configured by using one or more of the various processors as a hardware structure.

Furthermore, specifically, an electric circuit (circuitry) obtained by combining circuit elements, such as semiconductor elements, can be used as the hardware structure of the various processors.

What is claimed is:

1. An image processing device comprising at least one processor, wherein the processor is configured to:
    acquire, from storage coupled to the processor, two radiographic images based on radiation which has different energy distributions and has been transmitted through a subject including a soft part and a bone part, the two radiographic images being a first radiographic image having a low energy distribution and a second radiographic image having a high energy distribution; and
    determine a body thickness of the subject for each pixel of the first radiographic image, the second radiographic image, or a low-frequency radiographic image derived from the first radiographic image or the second radiographic image;
    remove scattered ray components in the first radiographic image and the second radiographic image;
    derive an initial value of a thickness of the soft part and an initial value of a thickness of the bone part on the basis of the body thickness of the subject;
    derive initial values of an attenuation coefficient of the soft part for each of the different energy distributions;
    derive initial values of an attenuation coefficient of the bone part for each of the different energy distributions;
    derive a subsequent value of the thickness of the soft part and a subsequent value of a thickness of the bone part;
    using the subsequent value of the thickness of the soft part and the subsequent value of the thickness of the bone part, derive subsequent values of the attenuation coefficient of the soft part for each of the different energy distributions and derive subsequent values of the attenuation coefficient of the bone part for each of the different energy distributions;
    among initial and subsequent values for the attenuation coefficient of the soft part for each of the different energy distributions and for the attenuation coefficient of the bone part for each of the different energy distributions, determine final values of the attenuation coefficient of the bone part and final values of the attenuation coefficient of the soft part at which a difference between $\{\mu_s \times t_s + \mu_b \times t_b\}$ and each pixel value of the radiographic image for each of the different energy distributions is minimized or at which the difference is less than a predetermined threshold value for each of the first radiographic image and the second radiographic image, wherein μs is a value of an attenuation coefficient of the soft part, ts is a thickness of the soft part, μb is an attenuation coefficient of the bone part, and tb is a thickness of the bone part;

determine a first weighting coefficient based on a ratio of the final values of the attenuation coefficient of the bone part, and determine a second weighting coefficient based on a ratio of the final values of the attenuation coefficients of the soft part;

generate a soft part radiographic image by performing a subtraction process using the first radiographic image, the second radiographic image and the first weighting coefficient, wherein contrast from the bone part is accurately removed from the soft part radiographic image, such that shadows can be observed in the soft part without any interference from the bone part; and generate a bone part radiographic image by performing a subtraction process using the first radiographic image, the second radiographic image and the second weighting coefficient, wherein contrast from the soft part is accurately removed from the bone part radiographic image, such that shadows can be observed in the bone part without any interference from the soft part.

2. The image processing device according to claim 1, wherein the processor is configured to remove the scattered ray components included in the two radiographic images on the basis of radiation characteristics of an object interposed between the subject and detectors that acquire the two radiographic images.

3. The image processing device according to claim 1, wherein the two radiographic images are acquired by two detectors, wherein the two detectors are superimposed on each other and irradiated with the radiation transmitted through the subject at the same time.

4. An image processing method comprising:

acquiring, from storage coupled to the processor, two radiographic images based on radiation which has different energy distributions and has been transmitted through a subject including a soft part and a bone part, the two radiographic images being a first radiographic image having a low energy distribution and a second radiographic image having a high energy distribution; and determining a body thickness of the subject for each pixel of the first radiographic image, the second radiographic image, or a low-frequency radiographic image derived from the first radiographic image or the second radiographic image;

removing scattered ray components in the first radiographic image and the second radiographic image;

deriving an initial value of a thickness of the soft part and an initial value of a thickness of the bone part on the basis of the body thickness of the subject;

deriving initial values of an attenuation coefficient of the soft part for each of the different energy distributions;

deriving initial values of an attenuation coefficient of the bone part for each of the different energy distributions;

deriving a subsequent value of the thickness of the soft part and a subsequent value of a thickness of the bone part;

using the subsequent value of the thickness of the soft part and the subsequent value of the thickness of the bone part, deriving subsequent values of the attenuation coefficient of the soft part for each of the different energy distributions and deriving subsequent values of the attenuation coefficient of the bone part for each of the different energy distributions;

among initial and subsequent values for the attenuation coefficient of the soft part for each of the different energy distributions and for the attenuation coefficient of the bone part for each of the different energy distributions, determining final values of the attenuation coefficient of the bone part and final values of the attenuation coefficient of the soft part at which a difference between and each pixel value of the radiographic image for each of the different energy distributions or at which the difference is less than a predetermined threshold value for each of the first radiographic image and the second radiographic image, wherein μs is a value of an attenuation coefficient of the soft part, ts is a thickness of the soft part, μb is an attenuation coefficient of the bone part, and tb is a thickness of the bone part;

determining a first weighting coefficient based on a ratio of the final values of the attenuation coefficient of the bone part, and determining a second weighting coefficient based on a ratio of the final values of the attenuation coefficients of the soft part;

generating a soft part radiographic image by performing a subtraction process using the first radiographic image, the second radiographic image and the first weighting coefficient, wherein contrast from the bone part is accurately removed from the soft part radiographic image, such that shadows can be observed in the soft part without any interference from the bone part; and generating a bone part radiographic image by performing a subtraction process using the first radiographic image, the second radiographic image and the second weighting coefficient, wherein contrast from the soft part is accurately removed from the bone part radiographic image, such that shadows can be observed in the bone part without any interference from the soft part.

5. A non-transitory computer-readable storage medium that stores an image processing program that is executable by a computer to perform processing comprising:

acquiring, from storage coupled to the processor, two radiographic images based on radiation which has different energy distributions and has been transmitted through a subject including a soft part and a bone part, the two radiographic images being a first radiographic image having a low energy distribution and a second radiographic image having a high energy distribution; and determining a body thickness of the subject for each pixel of the first radiographic image, the second radiographic image, or a low-frequency radiographic image derived from the first radiographic image or the second radiographic image;

removing scattered ray components in the first radiographic image and the second radiographic image;

deriving an initial value of a thickness of the soft part and an initial value of a thickness of the bone part on the basis of the body thickness of the subject;

deriving initial values of an attenuation coefficient of the soft part for each of the different energy distributions;

deriving initial values of an attenuation coefficient of the bone part for each of the different energy distributions;

deriving a subsequent value of the thickness of the soft part and a subsequent value of a thickness of the bone part;

using the subsequent value of the thickness of the soft part and the subsequent value of the thickness of the bone part, deriving subsequent values of the attenuation coefficient of the soft part for each of the different energy distributions and deriving subsequent values of the attenuation coefficient of the bone part for each of the different energy distributions;

among initial and subsequent values for the attenuation coefficient of the soft part for each of the different energy distributions and for the attenuation coefficient of the bone part for each of the different energy distributions, determining final values of the attenuation coefficient of the bone part and final values of the attenuation coefficient of the soft part at which a difference between and each pixel value of the radiographic image for each of the different energy distributions or at which the difference is less than a predetermined threshold value for each of the first radiographic image and the second radiographic image, wherein μs is a value of an attenuation coefficient of the soft part, ts is a thickness of the soft part, μb is an attenuation coefficient of the bone part, and tb is a thickness of the bone part;

determining a first weighting coefficient based on a ratio of the final values of the attenuation coefficient of the bone part, and determining a second weighting coefficient based on a ratio of the final values of the attenuation coefficients of the soft part;

generating a soft part radiographic image by performing a subtraction process using the first radiographic image, the second radiographic image and the first weighting coefficient, wherein contrast from the bone part is accurately removed from the soft part radiographic image, such that shadows can be observed in the soft part without any interference from the bone part; and generating a bone part radiographic image by performing a subtraction process using the first radiographic image, the second radiographic image and the second weighting coefficient, wherein contrast from the soft part is accurately removed from the bone part radiographic image, such that shadows can be observed in the bone part without any interference from the soft part.

* * * * *